(12) United States Patent
Sakai

(10) Patent No.: US 8,994,542 B2
(45) Date of Patent: Mar. 31, 2015

(54) BIOLOGICAL SIGNAL PROCESSOR

(71) Applicant: Tanita Corporation, Tokyo (JP)

(72) Inventor: Yoshio Sakai, Saitama (JP)

(73) Assignee: Tanita Corporation, Tokyo (JP)

( * ) Notice: Subject to any disclaimer, the term of this patent is extended or adjusted under 35 U.S.C. 154(b) by 133 days.

(21) Appl. No.: 13/782,596

(22) Filed: Mar. 1, 2013

(65) Prior Publication Data

US 2013/0278429 A1 Oct. 24, 2013

(30) Foreign Application Priority Data

Apr. 19, 2012 (JP) ................................. 2012-095376

(51) Int. Cl.
*G08B 21/00* (2006.01)
*G08B 21/18* (2006.01)
*A61B 5/00* (2006.01)
*A61B 5/11* (2006.01)

(52) U.S. Cl.
CPC ............ *G08B 21/185* (2013.01); *A61B 5/6892* (2013.01); *A61B 5/1113* (2013.01); *A61B 5/4809* (2013.01); *A61B 5/7225* (2013.01); *A61B 2560/0276* (2013.01); *A61B 2562/0204* (2013.01); *A61B 2562/0247* (2013.01)
USPC ........................................ 340/635; 340/573.1

(58) Field of Classification Search
CPC ..................... A61B 5/6892; A61B 2562/0247; G08B 21/0461; G08B 21/22
See application file for complete search history.

(56) References Cited

U.S. PATENT DOCUMENTS

| 4,686,999 | A | 8/1987 | Snyder et al. |
| 2006/0152378 | A1 | 7/2006 | Lokhorst et al. |
| 2008/0132808 | A1* | 6/2008 | Lokhorst et al. ............... 600/595 |
| 2009/0299421 | A1* | 12/2009 | Sawchuk .......................... 607/4 |
| 2012/0056747 | A1* | 3/2012 | Stadlthanner et al. ..... 340/573.4 |

FOREIGN PATENT DOCUMENTS

| CN | 86106763 A | 4/1988 |
| CN | 102317982 A | 1/2012 |

(Continued)

OTHER PUBLICATIONS

Extended European Partial Search Report for EP Application No. 13001254.5, Apr. 16, 2014.

(Continued)

*Primary Examiner* — Travis Hunnings

(57) ABSTRACT

A biological signal processor includes a sensor unit 2 that is usable with a mattress, measures biological displacement of a subject on the mattress, and outputs a measurement signal indicative of a measurement result, a signal processing unit 7 that amplifies the measurement signal with a plurality of different gains and outputs respective output signals, an AD converting unit 8 that performs AD conversion on the respective output signals to obtain level values and outputs the respective level values, and a determining unit 90 that determines that the sensor unit 2 is in an abnormal condition in case where a variation measure indicative of variation degree in level value corresponding to an output signal amplified with a minimum gain among the respective level values is equal to or less than a predetermined value.

10 Claims, 14 Drawing Sheets

(56) References Cited

FOREIGN PATENT DOCUMENTS

| | | | |
|---|---|---|---|
| CN | 203234723 U | | 10/2013 |
| JP | H04-28344 A | | 1/1992 |
| JP | 2008-206596 | | 9/2008 |
| JP | 2008-259745 | | 10/2008 |
| JP | 2008-259745 A | | 10/2008 |
| WO | 86/05965 A1 | | 10/1986 |
| WO | WO 8605965 A1 | * | 10/1986 |
| WO | 2004/006768 A1 | | 1/2004 |
| WO | 2010/092517 A1 | | 8/2010 |

OTHER PUBLICATIONS

EPO, Partial European Search Report for European Patent Application No. 13001254.5, Jan. 8, 2014.

SIPO, Chinese Office Action for Chinese Patent Application No. 201310139595.4, Aug. 11, 2014.

SIPO, Chinese Search Report for Chinese Patent Application No. 201310139595.4, Aug. 11, 2014.

* cited by examiner

FIG.21

| Time | SD0 | SD1 | SD2 | SD3 | SD1/SD0 | SD2/SD0 | SD3/SD0 |
|---|---|---|---|---|---|---|---|
| 30 | 185.0 | 338.8 | 455.9 | 471.6 | 1.8 | 2.5 | 2.5 |
| 60 | 23.4 | 81.2 | 210.5 | 302.5 | 3.5 | 9.0 | 12.9 |
| 90 | 15.6 | 54.0 | 163.2 | 384.6 | 3.5 | 10.5 | 24.7 |
| 120 | 16.8 | 58.1 | 175.3 | 393.4 | 3.5 | 10.5 | 23.5 |
| 150 | 17.4 | 60.4 | 182.5 | 410.3 | 3.5 | 10.5 | 23.6 |
| 180 | 15.9 | 55.4 | 167.3 | 399.3 | 3.5 | 10.5 | 25.1 |
| 210 | 16.3 | 56.6 | 171.0 | 404.4 | 3.5 | 10.5 | 24.8 |
| 240 | 16.8 | 58.3 | 176.0 | 411.9 | 3.5 | 10.5 | 24.5 |
| 270 | 17.5 | 60.8 | 183.6 | 415.9 | 3.5 | 10.5 | 23.7 |
| 300 | 17.9 | 62.2 | 187.7 | 422.0 | 3.5 | 10.5 | 23.6 |

FIG.22

| Time | SD0 | SD1 | SD2 | SD3 | SD1/SD0 | SD2/SD0 | SD3/SD0 |
|---|---|---|---|---|---|---|---|
| 30 | 4.9 | 16.9 | 51.0 | 152.0 | 3.4 | 10.4 | 31.0 |
| 60 | 1.6 | 5.5 | 16.6 | 49.9 | 3.4 | 10.3 | 31.1 |
| 90 | 1.8 | 6.1 | 18.3 | 55.5 | 3.4 | 10.2 | 31.0 |
| 120 | 1.5 | 5.0 | 15.2 | 45.9 | 3.4 | 10.2 | 31.0 |
| 150 | 2.3 | 7.9 | 23.9 | 72.4 | 3.4 | 10.4 | 31.3 |
| 180 | 3.0 | 10.3 | 31.0 | 90.6 | 3.4 | 10.4 | 30.2 |
| 210 | 3.8 | 13.0 | 39.4 | 93.4 | 3.5 | 10.5 | 24.8 |
| 240 | 2.1 | 7.4 | 22.4 | 67.9 | 3.5 | 10.4 | 31.6 |
| 270 | 1.5 | 5.3 | 15.9 | 48.0 | 3.5 | 10.5 | 31.8 |
| 300 | 1.3 | 4.5 | 13.7 | 41.3 | 3.4 | 10.3 | 31.0 |

FIG.23

| Time | SD0 | SD1 | SD2 | SD3 | SD1/SD0 | SD2/SD0 | SD3/SD0 |
|---|---|---|---|---|---|---|---|
| 30 | 0.5 | 0.7 | 2.1 | 6.1 | 1.4 | 4.2 | 12.4 |
| 60 | 0.0 | 0.6 | 1.5 | 4.2 | | | |
| 90 | 0.2 | 0.4 | 0.9 | 2.3 | 1.5 | 3.7 | 9.5 |
| 120 | 0.5 | 0.1 | 0.8 | 1.6 | 0.3 | 1.5 | 3.2 |
| 150 | 0.2 | 0.5 | 0.9 | 2.2 | 2.2 | 4.1 | 10.1 |
| 180 | 0.0 | 0.1 | 0.7 | 1.4 | | | |
| 210 | 0.0 | 0.4 | 0.6 | 1.0 | | | |
| 240 | 0.0 | 0.5 | 0.6 | 0.0 | | | |
| 270 | 0.0 | 0.2 | 0.7 | 1.3 | | | |
| 300 | 0.0 | 0.1 | 0.6 | 0.9 | | | |

| Time | SD0 | SD1 | SD2 | SD3 | SD1/SD0 | SD2/SD0 | SD3/SD0 |
|---|---|---|---|---|---|---|---|
| 30 | 243.5 | 444.4 | 487.6 | 503.1 | 1.8 | 2.0 | 2.1 |
| 60 | 256.6 | 448.6 | 492.4 | 506.7 | 1.7 | 1.9 | 2.0 |
| 90 | 235.6 | 438.2 | 487.9 | 501.4 | 1.9 | 2.1 | 2.1 |
| 120 | 226.5 | 427.3 | 485.2 | 500.3 | 1.9 | 2.1 | 2.2 |
| 150 | 235.3 | 424.0 | 484.7 | 504.9 | 1.8 | 2.1 | 2.1 |
| 180 | 302.3 | 461.7 | 494.3 | 507.9 | 1.5 | 1.6 | 1.7 |
| 210 | 284.2 | 457.7 | 493.6 | 504.8 | 1.6 | 1.7 | 1.8 |
| 240 | 275.6 | 446.2 | 491.7 | 505.0 | 1.6 | 1.8 | 1.8 |
| 270 | 248.6 | 429.3 | 481.6 | 498.5 | 1.7 | 1.9 | 2.0 |
| 300 | 282.7 | 453.6 | 486.6 | 503.2 | 1.6 | 1.7 | 1.8 |

FIG.24

BIOLOGICAL SIGNAL PROCESSOR

CROSS-REFERENCES TO RELATED APPLICATION

This application claims priority from Japanese Patent Application Serial No. 2012-095376 filed Apr. 19, 2012, the content of which is incorporated herein by reference in its entirety.

TECHNICAL FIELD

The present invention relates to a biological signal processor that processes a signal based on subject's biological displacement (such as a respiration, a heartbeat, a pulse, and a body motion).

BACKGROUND

In recent years, a biological signal processor that processes a signal based on subject's biological displacement (such as a respiration, a heartbeat, a pulse, and a body motion) has been proposed. The biological signal processor is, for example, applied to a sleep state measuring apparatus that measures a subject's sleep state. In the sleep state measuring apparatus, although starting the measurement of the sleep state requires a start command to the apparatus, a problem arises in that since sleeping is everyday behavior, the subject tends to forget the command operation (such as switch operation). When the biological signal processor is used, without any special operation on the sleep state measuring apparatus by the subject, it is possible to determine that the subject is in bed thereby performing a sleep state measurement. For example, Japanese Patent Application Publication No. 2008-259745 discloses a technique in which a mat-type sensor installed under bedding is used so as to acquire a signal based on biological displacement such as a body motion, a respiration, and a heartbeat from an output of the sensor. The mat-type sensor is a sensor that uses air or water for detecting internal pressure variation of the mattress.

SUMMARY

However, a sensor output (sensitivity) significantly changes depending on various factors such as difference between subjects, differences in sleeping posture, differences in bedding, or the like. Accordingly, before the measurement, adjustment and setting for the sensor output (sensitivity) are needed. In the mat-type sensor using air, water, or similar medium, a problem arises in that aged deterioration does not allow acquiring an appropriate output. For example, reduction in content due to air leakage, water evaporation etc. changes the sensor output. However, the user has difficulty being aware of this change. The present invention has been made in view of the above-described circumstances, and it is an object of the present invention to provide a biological signal processor that automatically performs the adjustment and the setting for the sensor output (sensitivity) before the measurement and allows the appropriate determination of sensor failure etc.

A biological signal processor according to the present invention includes a sensor unit that can be used with a mattress and that measures biological displacement of a subject on the mattress thereby outputting a measurement signal indicative of a measurement result, a signal processing unit that amplifies the measurement signal with a plurality of different gains and outputs respective output signals, an AD converting unit that performs AD conversion on the respective output signals to obtain level values and outputs the respective level values, and a determining unit that determines that the sensor unit is in an abnormal condition in case where a variation measure indicative of variation degree in a level value corresponding to an output signal amplified with a minimum gain among the respective level values is equal to or less than a predetermined value. Herein, "biological displacement" is physical displacement (such as increase and decrease in volume) caused by subject's biological activity (such as a respiration, a heartbeat, a pulse, a body motion).

With the above-described configuration, when the variation degree in a level value corresponding to the output signal amplified with the minimum gain among the level values that reflect the subject's biological displacement, is equal to or less than the predetermined value, the sensor unit is determined to be abnormal. Accordingly, it is possible to appropriately determine a failure such as disconnection of the sensor, aged deterioration etc. due to an abnormal sensor output.

In an embodiment, the determining unit uses the level value corresponding to the output signal amplified with the minimum gain among the respective level values as a reference value. The determining unit calculates a ratio of a variation measure indicative of variation degree in a level value corresponding to an output signal amplified with another gain, to the variation measure indicative of variation degree in the reference value. Where a ratio of a variation measure indicative of variation degree in a level value corresponding to an output signal amplified with a predetermined gain, to the variation measure indicative of the variation degree in the reference value is within a predetermined value range with respect to a ratio of the predetermined gain to the minimum gain, the determining unit employs an output signal amplified with the predetermined gain as an output signal of the signal processing unit. The above-described configuration uses the level value corresponding to the output signal amplified with the minimum gain as the reference value, and compares the ratio of the variation degree in the level value corresponding to the output signal amplified with the predetermined gain to the variation degree in the reference value, with the ratio of the predetermined gain to the minimum gain. In the case where the ratios are within the predetermined value range, the output signal amplified with the predetermined gain is employed as the output signal of the signal processing unit. Accordingly, it is possible to perform a process based on a signal amplified with an appropriate gain without using a saturated signal.

In another embodiment, in case where the ratio of the variation measure indicative of the variation degree in a level value corresponding to the output signal amplified with each gain is not within the predetermined value range regarding the ratio of each gain to the minimum gain, the determining unit determines that the sensor unit is abnormal. With the above-described configuration, in case of any gain, where comparison result of the two ratios is not within the predetermined value, the sensor unit is determined to be abnormal. Accordingly, it is possible to appropriately determine a sensor output is abnormal due to aged deterioration etc.

In another embodiment, the biological signal processor further includes a detection unit that performs a biological information detection process based on an output signal of the signal processing unit employed by the determining unit. With the above-described configuration, a biological information detection process is appropriately performed, without using a saturated signal, based on the signal amplified with an appropriate gain.

In still another embodiment, the signal processing unit includes a plurality of analog circuits. With this configuration, among a plurality of analog circuits, an analog circuit with an appropriate gain can amplify the measurement signal.

In still another, the signal processing unit includes an analog circuit that allows switching between different gains. With this configuration, among a plurality of gains, an analog circuit with an appropriate gain can amplify the measurement signal.

In a still further embodiment, the variation measure indicative of the variation degree is a standard deviation. With this configuration, a failure of the sensor, occurrence of a saturated signal or similar can be appropriately determined.

Another biological signal processor according to an embodiment includes a sensor unit that can be used with a mattress and that measures biological displacement of a subject on the mattress, thereby outputting a measurement signal indicative of a measurement result, a signal processing unit that amplifies the measurement signal with a plurality of different gains and outputs respective output signals, an AD converting unit that performs AD conversion on the respective output signals to obtain level values and outputs the respective level values, and a determining unit that determines that the sensor unit is in an abnormal condition in case where the number of level values at a lower limit value per unit time corresponding to an output signal amplified with a minimum gain among the respective level values exceeds a specified value.

With this configuration, when the number of the level values corresponding to the output signal amplified with the predetermined gain at the lower limit value per unit time corresponding to the output signal amplified with the minimum gain exceeds the specified value, the sensor unit is determined to be abnormal. Accordingly, it is possible to appropriately determine that a sensor output is abnormal due to aged deterioration etc.

In a still further embodiment, the determining unit employs an output signal amplified with a predetermined gain as an output signal of the signal processing unit in case where the number of level values at an upper limit value per unit time corresponding to the output signal amplified with the predetermined gain falls below a specified value. With this configuration, without using a saturated signal, the process can be appropriately performed based on the signal amplified with an appropriate gain.

In a still further embodiment, the determining unit determines that the sensor unit is in an abnormal condition in case where the number of level values at an upper limit value per unit time corresponding to the output signal amplified with each gain exceeds a specified value. With this configuration, it is possible to appropriately determine that a sensor output is abnormal due to aged deterioration etc.

BRIEF DESCRIPTION OF DRAWINGS

Other features and advantages of the present biological signal processor will be apparent from the ensuing description, taken in conjunction with the accompanying drawings, in which:

FIG. 21 is a table illustrating standard deviations of the respective input signals illustrated in FIG. 5 to FIG. 8 and ratios of respective standard deviations of input signals other than a reference signal with a standard deviation of the reference signal;

FIG. 22 is a table illustrating standard deviations of the respective input signals illustrated in FIG. 9 to FIG. 12 and ratios of respective standard deviations of input signals other than a reference signal with a standard deviation of the reference signal;

FIG. 23 is a table illustrating standard deviations of the respective input signals illustrated in FIG. 13 to FIG. 16 and ratios of respective standard deviations of input signals other than a reference signal with a standard deviation of the reference signal;

FIG. 24 is a table illustrating standard deviations of the respective input signals illustrated in FIG. 17 to FIG. 20 and ratios of respective standard deviations of input signals other than a reference signal with a standard deviation of the reference signal.

DESCRIPTION OF EMBODIMENTS

1. Configuration of a Sleep State Measuring Apparatus

Figure 1:
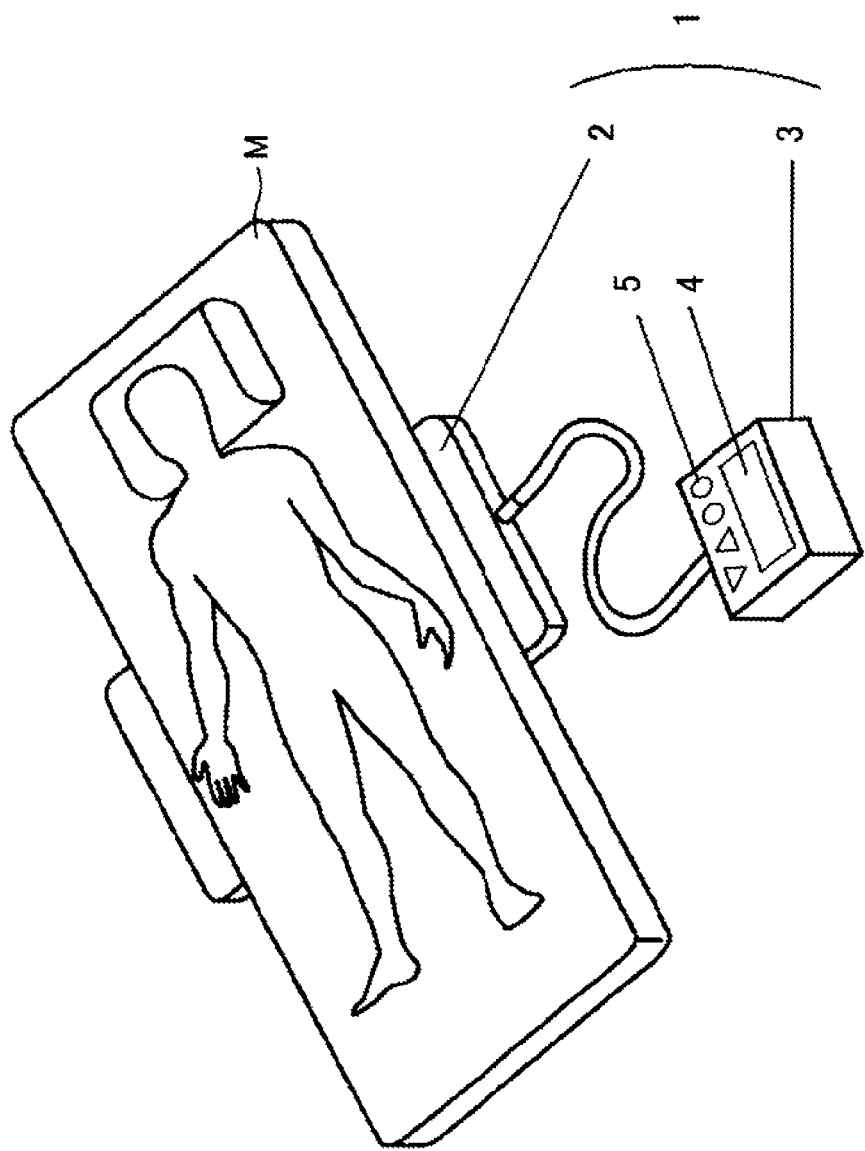
FIG. 1 is an external view illustrating an in-use condition of a sleep state measuring apparatus according to an embodiment of the present invention.

FIG. 1 is an external view illustrating an in-use condition of a sleep state measuring apparatus 1 according to an embodiment of the present invention. The sleep state measuring apparatus 1 measures a sleep state of a subject lying on a mattress (such as a bed mattress and a futon mattress) M. As illustrated in FIG. 1, the sleep state measuring apparatus 1 includes a sensor unit 2 and a main unit 3.

The sensor unit 2 is a component usable with the mattress M, for example, as illustrated in FIG. 1, and is arranged under the mattress M. The sensor unit 2 measures (detects), using a microphone (such as a capacitor microphone), subject's biological displacement (such as a respiration, a heartbeat, a pulse, and a body motion) on the mattress M as a pressure variation of incompressible fluid loaded into the sensor unit 2 to output a measurement signal indicative of a measurement result.

A main unit 3 is connected to the sensor unit 2, and performs an in-bed determining operation and a sleep state measurement operation based on the measurement signal output from the sensor unit 2. The main unit 3 includes a display unit 4 and an operating unit 5. The display unit 4 displays a measured sleep state etc. The operating unit 5 is used for an operation performed by a subject. The operating unit 5 has a power switch.

Figure 2:
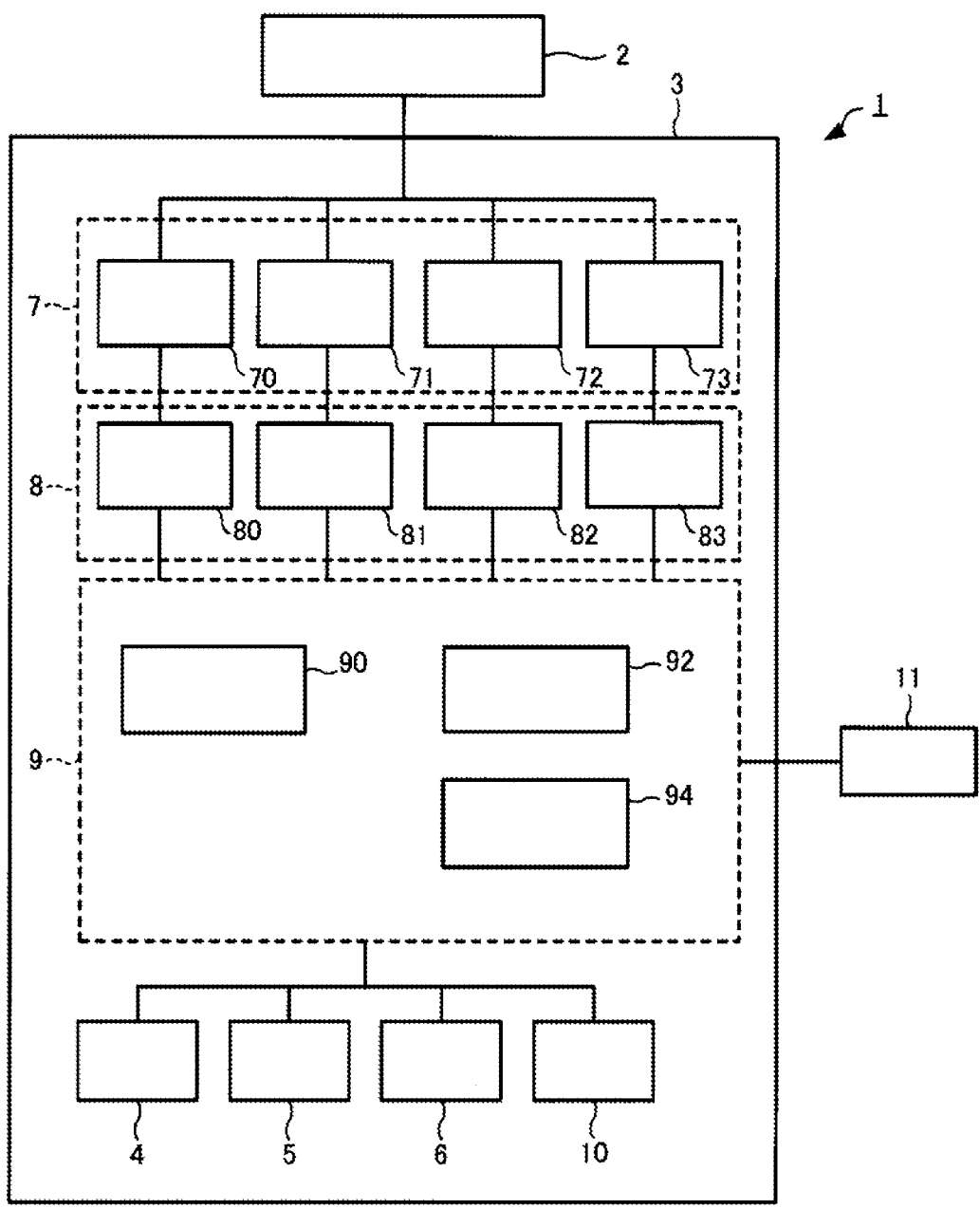
FIG. 2 is a block diagram illustrating a configuration of the sleep state measuring apparatus.

FIG. 2 is a block diagram illustrating a configuration of the sleep state measuring apparatus 1. The main unit 3 includes the display unit 4, the operating unit 5, an external output unit 6, a signal processing unit 7, an AD converting unit 8, Central Processing Unit (CPU) 9, and a storage unit 10. The main unit 3 is connected to a power supply 11. The external output unit 6 is an interface that externally outputs an in-bed determination result, a sleep state determination result, a failure determination result for the sensor unit. For example, the external output unit 6 may employ a memory card slot or a USB interface, or may also employ a wireless communication interface such as WI-FI (registered trademark) and BLUETOOTH (registered trademark). The storage unit 10 is a storage medium in which a program and data used when the in-bed determination and the sleep state determination are performed, is stored. For example, the storage unit 10 is a ROM, a RAM, or their combination.

The signal processing unit 7 includes a first amplifier 70, a second amplifier 71, a third amplifier 72, and a fourth amplifier 73. The first amplifier 70 amplifies the measurement signal output from the sensor unit 2 with a gain of 1× and outputs a signal to the CPU 9 as a first output signal. The second amplifier 71 amplifies the measurement signal output from the sensor unit 2 with a gain of 3.4× and outputs a signal to the CPU 9 as a second output signal. The third amplifier 72 amplifies the measurement signal output from the sensor unit 2 with a gain of 10.2× and outputs A signal to the CPU 9 as a third output signal. The fourth amplifier 73 amplifies the measurement signal output from the sensor unit 2 with a gain of 31× and outputs A signal to the CPU 9 as a fourth output signal.

The AD converting unit 8 includes a first AD converting unit 80, a second AD converting unit 81, a third AD converting unit 82, and a fourth AD converting unit 83. The first AD converting unit 80 outputs, to a determining unit 90, a first level value obtained by AD conversion of the first output signal, which is supplied from the first amplifier 70 of the signal processing unit 7. The second AD converting unit 81 outputs, to the determining unit 90, a second level value obtained by AD conversion of the second output signal, which is supplied from the second amplifier 71 of the signal processing unit 7. The third AD converting unit 82 outputs, to the determining unit 90, a third level value obtained by AD conversion of the third output signal, which is supplied from the third amplifier 72 of the signal processing unit 7. The fourth AD converting unit 83 outputs, to the determining unit 90, a fourth level value obtained by AD conversion of the fourth output signal, which is supplied from the fourth amplifier 73 of the signal processing unit 7.

The CPU 9 includes the determining unit 90, a biological information detection unit 92, and a notification processing unit 94. The determining unit 90 performs the failure determination of the sensor unit 2 or determination of a level value to be used (further details of which are described below) based on standard deviations SD0, SD1, SD2, and SD3 that indicate respective variation degrees of the first level value, the second level value, the third level value, and the fourth level value or based on the first level value, the second level value, the third level value and the fourth level value. A level value determined as the level value to be used by the determining unit 90 is output to the biological information detection unit 92. The biological information detection unit 92 calculates subject's biological information based on the level value and measures a sleep state of the subject based on the subject's biological information. The measured sleep state, the measured failure determination result etc. are output to the notification processing unit 94. The notification processing unit 94 outputs the measured sleep state, the measured failure determination result etc. to the display unit 4 and the external output unit 6. The determining unit 90, the biological information detection unit 92, and the notification processing unit 94 are function blocks achieved by the CPU 9 executing a computer program stored in the storage unit 10 and functioning in accordance with the computer program.

2. Entire Operation

Figure 3:
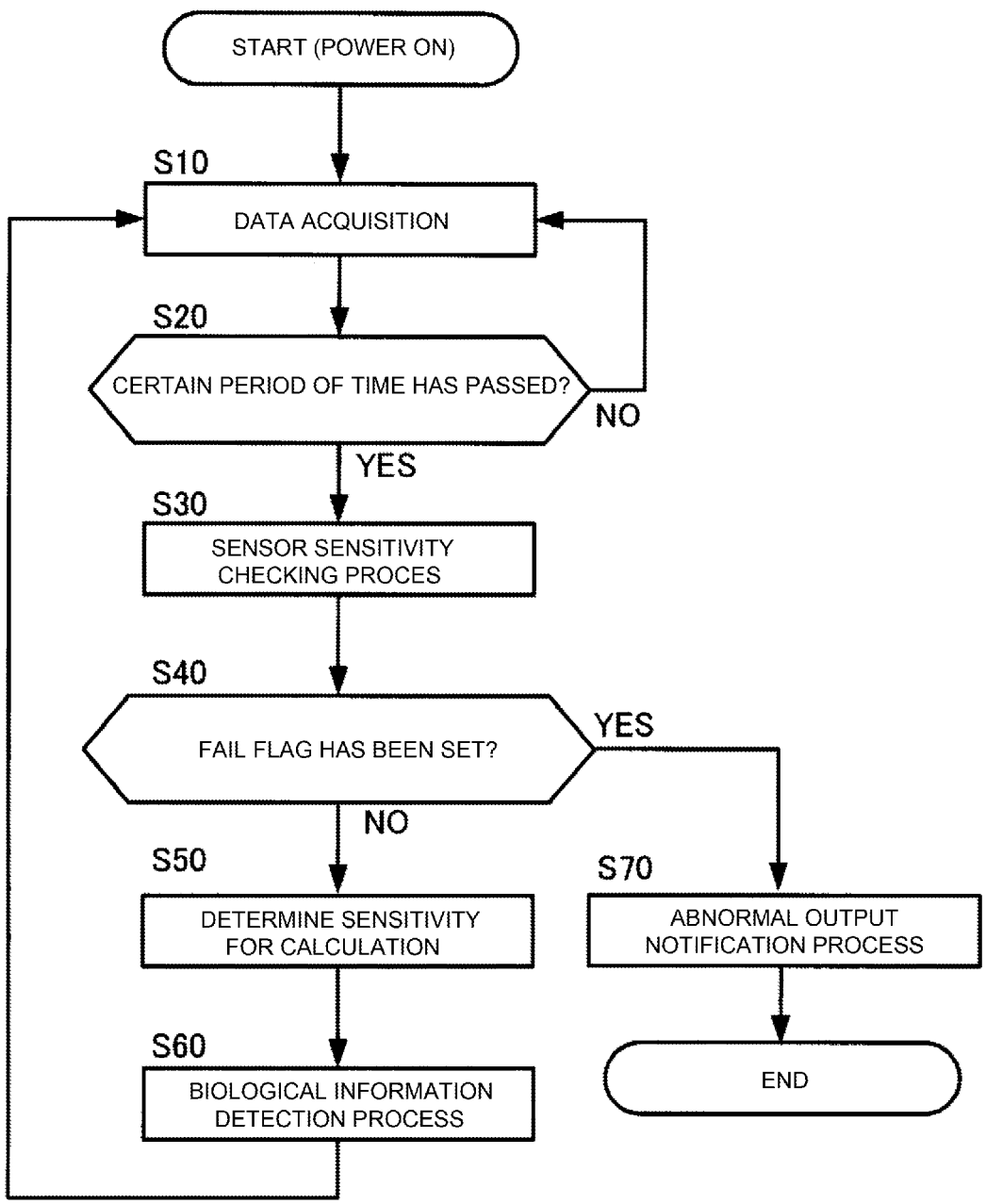
FIG. 3 is a flowchart illustrating an entire operation of the sleep state measuring apparatus.
Figure 4:
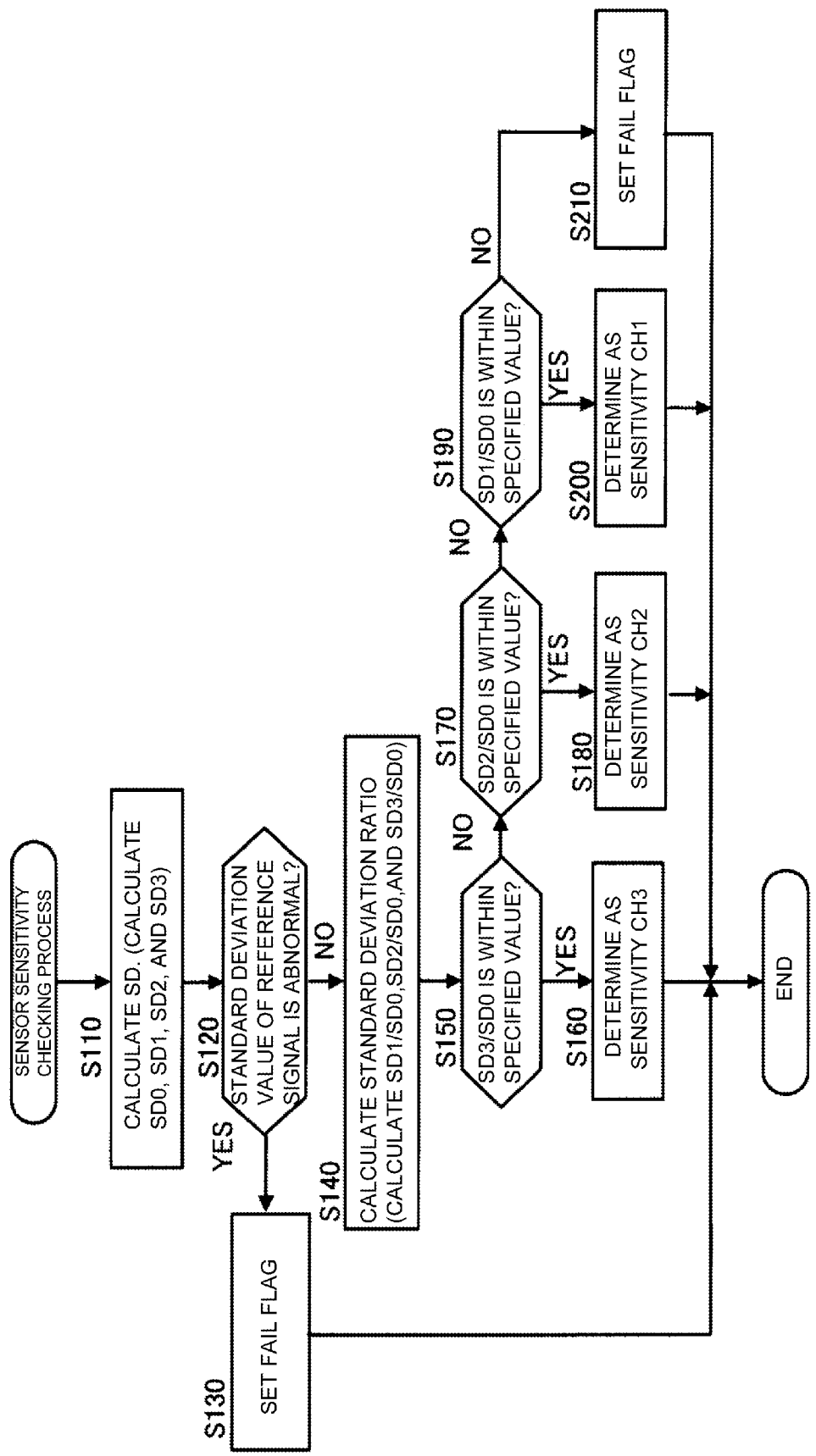
FIG. 4 is a flowchart illustrating a sensor sensitivity checking operation of the sleep state measuring apparatus.
Figure 5:
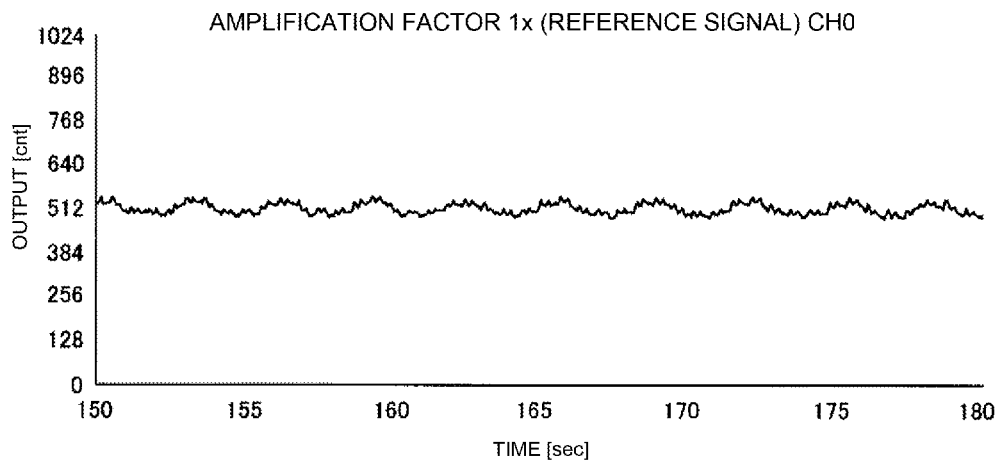
FIG. 5 is a graph illustrating an exemplary transition of an input signal from a first amplifier where a subject is in bed.

Next, an entire operation of the sleep state measuring apparatus 1 according to the embodiment will be described by referring to a flowchart of FIG. 3. Turning on the power supply of the sleep state measuring apparatus 1 makes the sleep state measuring apparatus 1 to start operating. The output signals of the sensor unit 2 are amplified with the respective gains by the first amplifier 70, the second amplifier 71, the third amplifier 72, and the fourth amplifier 73. The amplified signals are AD converted by the first AD converting unit 80, the second AD converting unit 81, the third AD converting unit 82, and the fourth AD converting unit 83. The converted signals are input to the determining unit 90 as the first level value, the second level value, the third level value, and the fourth level value. Then, data acquisition is performed (S10).

The data acquisition is continued until a certain period of time (for example 30 seconds) passes (NO in S20, then return to S10). Where the certain period of time has passed (YES in S20), a sensor sensitivity checking process is performed based on the acquired data (S30). The sensor sensitivity checking process will be described in detail later. After the sensor sensitivity checking process, it is determined whether or not a fail flag is set (S40). Where the fail flag is not set and the sensor unit 2 operates normally (NO in S40), a sensitivity (gain) determined by the sensor sensitivity checking process is determined as a sensitivity (gain) for calculation (S50).

The biological information detection unit 92 receives the output signal from the amplifier with the sensitivity (gain) set for calculation as a level value AD converted by a corresponding AD converting unit, and detects biological information such as a body motion, a respiration, a heartbeat of the subject based on the level value (S60). Subsequently, based on the detected biological information, determination of an in-bed state, determination of a sleep state, and similar determination of the subject are performed. Hereinafter, the above-described process is continued until the power supply is turned off.

On the other hand, where the fail flag is set after the sensor sensitivity checking process (YES in S40), the notification processing unit 94 displays a failure state of the sensor unit 2 on the display unit 4 and notifies about the failure state of the sensor unit 2 to outside via the external output unit 6 (S70), as an abnormal output notification process. The sleep state measuring apparatus 1 then terminates the process.

3. Sensor Sensitivity Checking Operation

Next, the sensor sensitivity checking operation according to the embodiment will be described by referring to a flowchart of FIG. 4 and FIG. 5 to FIG. 24. The sleep state measuring apparatus 1 of the embodiment includes four kinds of amplifiers with different amplification factors (gains). As one example, the amplification factor (gain) of the first amplifier 70 is set to 1×, the amplification factor (gain) of the second amplifier 71 is set to 3.4×, the amplification factor (gain) of the third amplifier 72 is set to 10.2×, and the amplification factor (gain) of the fourth amplifier 73 is set to 31×.

The output signals of the first amplifier 70, the second amplifier 71, the third amplifier 72, and the fourth amplifier 73 are input, via the first AD converting unit 80 through the fourth AD converting unit 83 connected to the respective amplifiers, to input ports of the determining unit 90 that are CH0, CH1, CH2 and CH3.

FIGS. 5, 6, 7, and 8 illustrate examples of the respective input signals of CH0, CH1, CH2, and CH3 where the subject lies on the mattress M. FIGS. 9, 10, 11, and 12 illustrate examples of the respective input signals of CH0, CH1, CH2, and CH3 where the power supply of the sleep state measuring apparatus 1 is turned on but the subject is not lying on the mattress M. FIGS. 13, 14, 15, and 16 illustrate examples of the respective input signals of CH0, CH1, CH2, and CH3 in failure states such as disconnection. FIGS. 17, 18, 19, and 20 illustrate examples of the respective input signals of CH0, CH1, CH2, and CH3 in failure states where vibrations are severe.

In the embodiment, the determining unit 90 uses the input signal from the first amplifier 70 with the smallest amplification factor (gain) of 1× as a reference signal. Subsequently, standard deviations of the respective input signals from the second amplifier 71, the third amplifier 72, and the fourth amplifier 73 including the reference signal are calculated (S110). The standard deviation of the reference signal is represented as SD0, the standard deviation of the input signal from the second amplifier 71 is represented as SD1, the standard deviation of the input signal from the third amplifier 72 is represented as SD2, and the standard deviation of the input signal from the fourth amplifier 73 is represented as SD3.

The standard deviations SD0, SD1, SD2, and SD3 are variation measures that indicate variation degrees of the respective input signals, and have a certain level of value respectively even where the power supply of the sleep state measuring apparatus 1 is turned on but the subject is not lying on the mattress M. This is because, as illustrated in FIGS. 9-12, noise such as subtle vibration at the installation site causes changing the respective input signals even where the subject is not lying on the mattress M.

FIG. 21 illustrates values of the standard deviations SD0, SD1, SD2, and SD3 for each certain period of time (30 seconds) in the cases of FIGS. 5-8 (where the subject is lying on the mattress M). FIG. 22 illustrates values of the standard deviations SD0, SD1, SD2, and SD3 for each certain period of time (30 seconds) in the cases of FIGS. 9-12 (where the subject is not lying on the mattress M). FIG. 23 illustrates values of the standard deviations SD0, SD1, SD2, and SD3 for each certain period of time (30 seconds) in the cases of FIGS. 13-16 (where the sensor unit 2 has a failure such as disconnection). FIG. 24 illustrates values of the standard deviations SD0, SD1, SD2, and SD3 for each certain period of time (30 seconds) in the cases of FIGS. 17-20 (in abnormal cases with heavy vibration).

Figure 9:
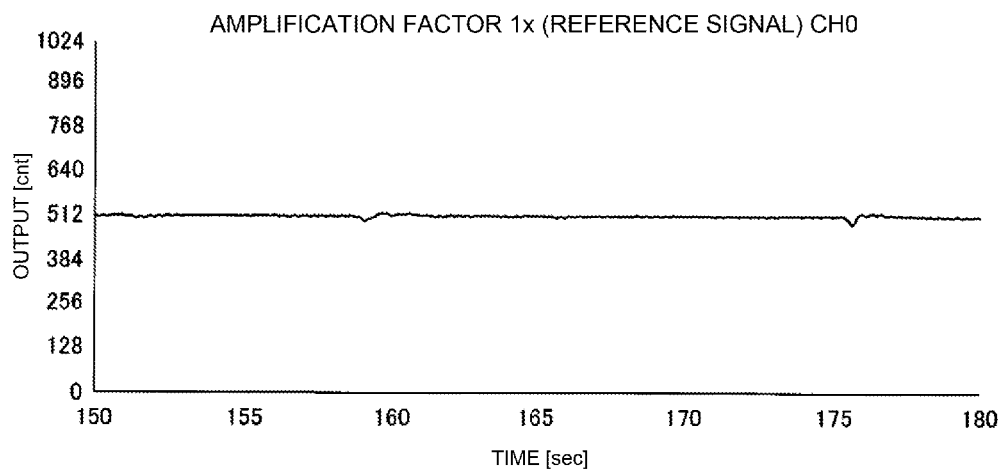
FIG. 9 is a graph illustrating an exemplary transition of an input signal from the first amplifier where the subject is not in bed.
Figure 10:
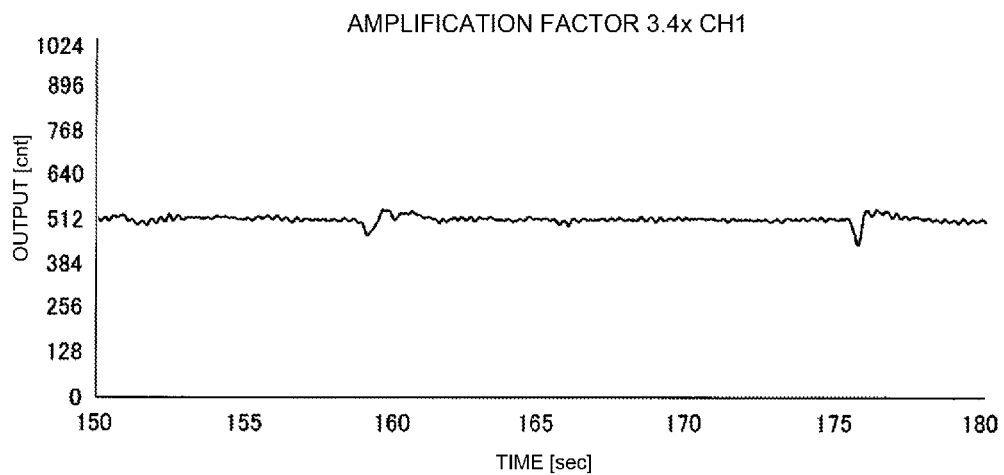
FIG. 10 is a graph illustrating an exemplary transition of an input signal from the second amplifier where the subject is not in bed.
Figure 11:
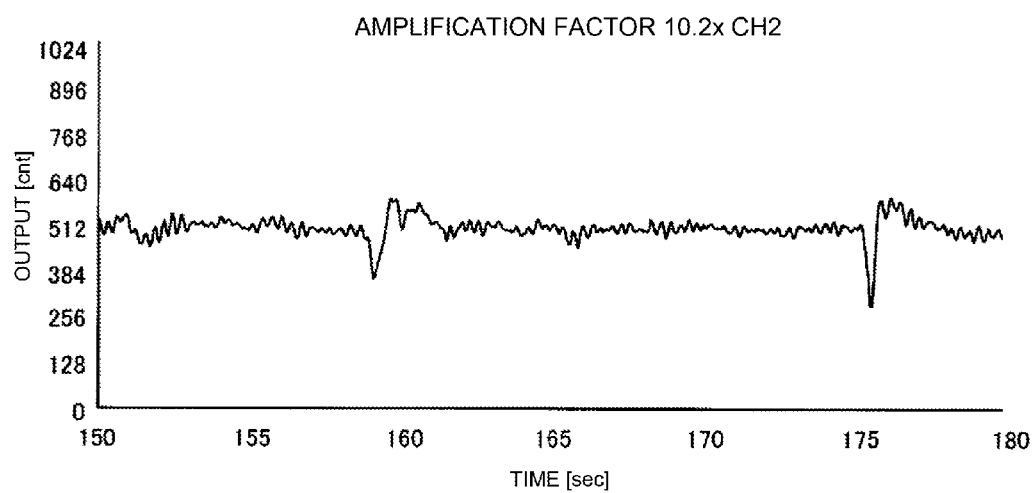
FIG. 11 is a graph illustrating an exemplary transition of an input signal from the third amplifier where the subject is not in bed.
Figure 12:
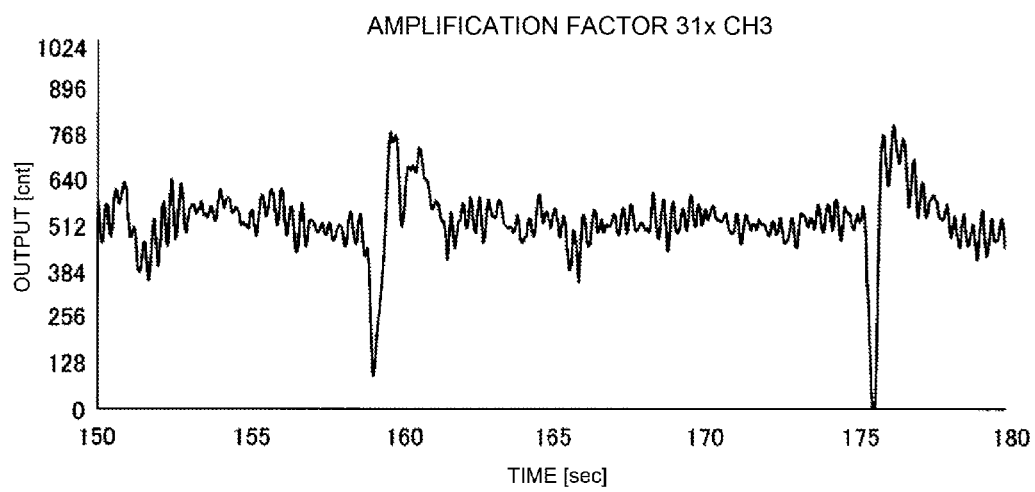
FIG. 12 is a graph illustrating an exemplary transition of an input signal from the fourth amplifier where the subject is not in bed.
Figure 13:
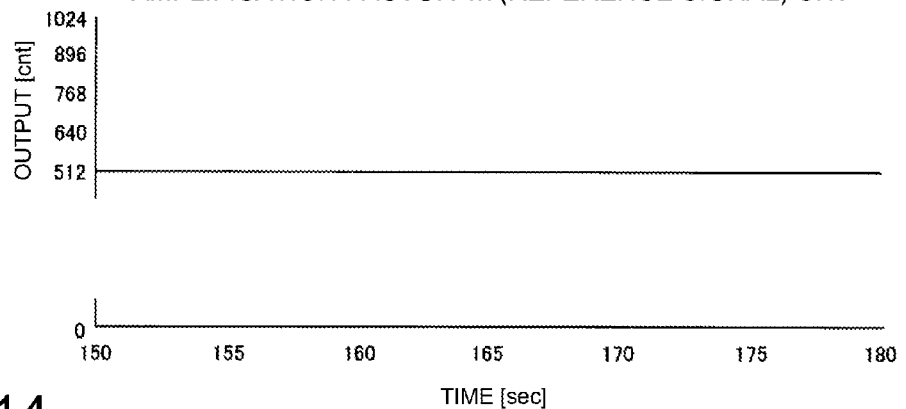
FIG. 13 is a graph illustrating an exemplary transition of an input signal from the first amplifier where a sensor is disconnected.
Figure 14:
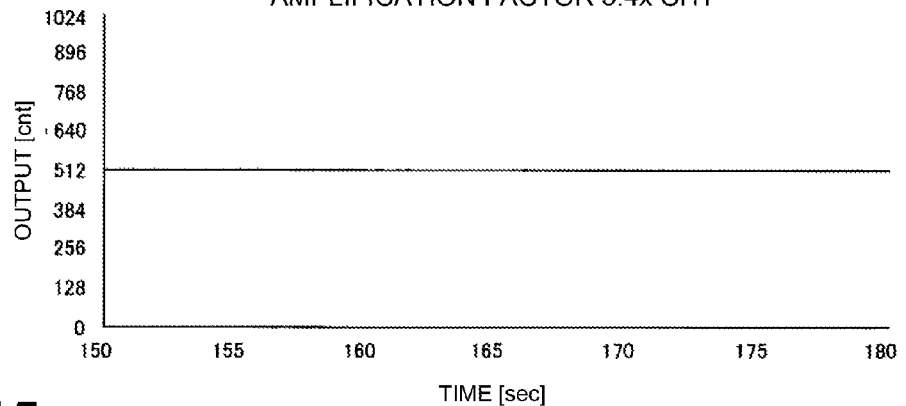
FIG. 14 is a graph illustrating an exemplary transition of an input signal from the second amplifier where a sensor is disconnected.
Figure 15:
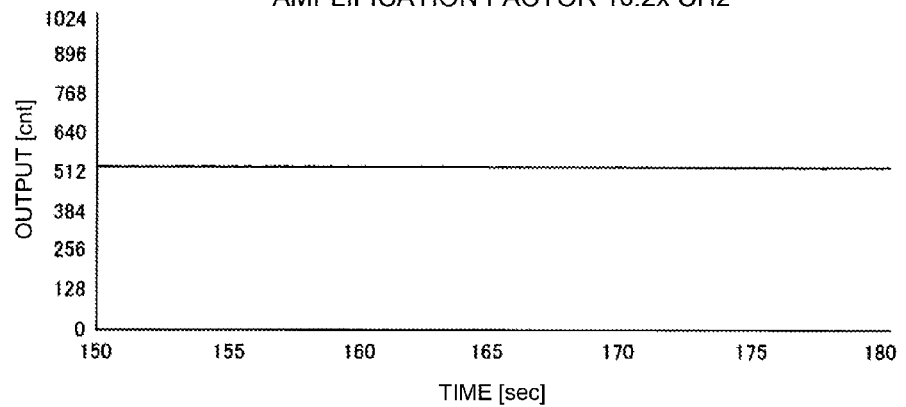
FIG. 15 is a graph illustrating an exemplary transition of an input signal from the third amplifier where a sensor is disconnected.
Figure 16:
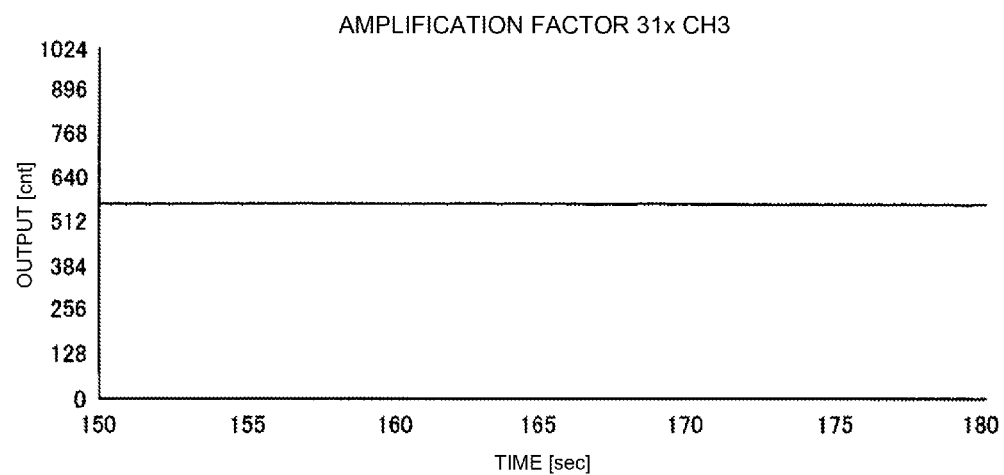
FIG. 16 is a graph illustrating an exemplary transition of an input signal from the fourth amplifier where a sensor is disconnected.
Figure 17:
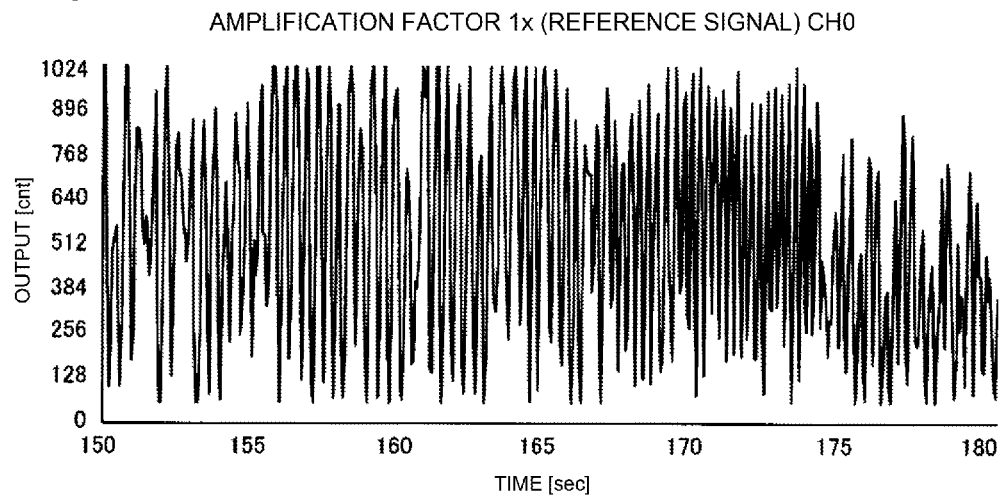
FIG. 17 is a graph illustrating an exemplary transition of an input signal from the first amplifier where a sensor output is abnormal.
Figure 18:
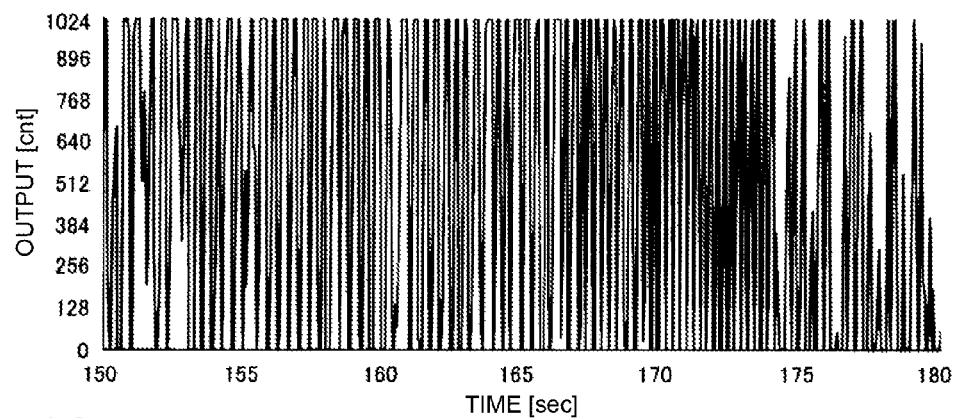
FIG. 18 is a graph illustrating an exemplary transition of an input signal from the second amplifier where a sensor output is abnormal.
Figure 19:
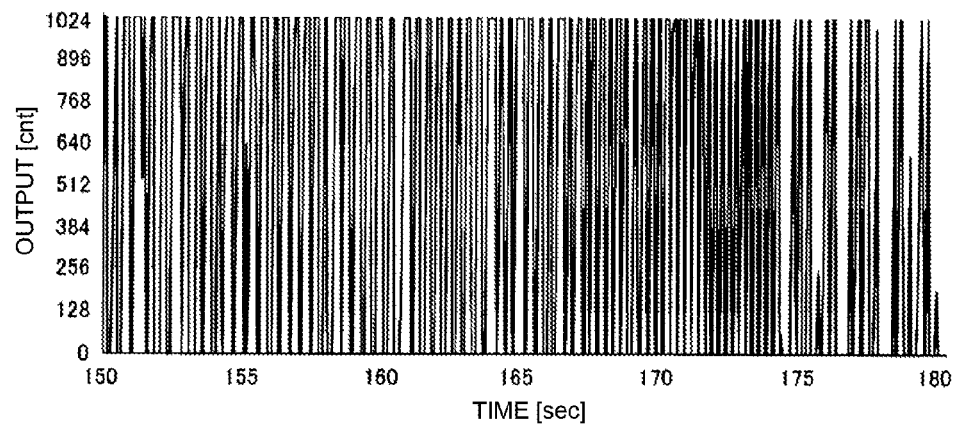
FIG. 19 is a graph illustrating an exemplary transition of an input signal from the third amplifier where a sensor output is abnormal.
Figure 20:
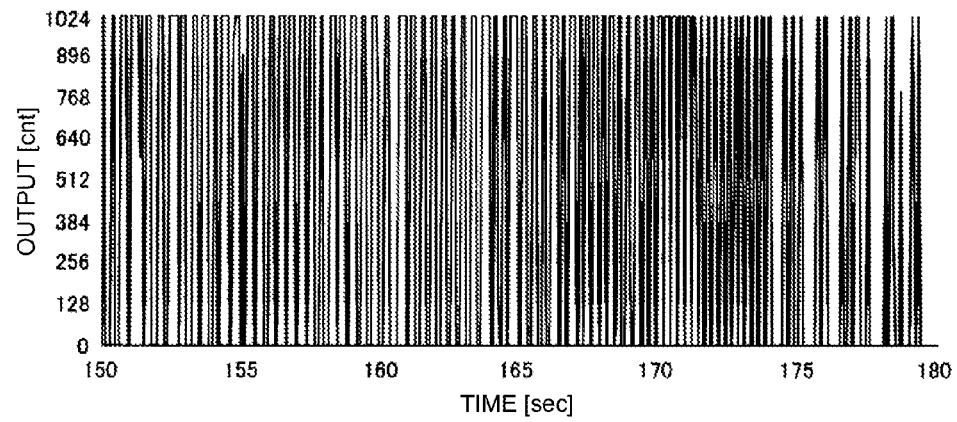
FIG. 20 is a graph illustrating an exemplary transition of an input signal from the fourth amplifier where a sensor output is abnormal.

In the sensor sensitivity checking process of the embodiment, after standard deviations of the respective input signals are calculated (S110), it is determined whether a value of the standard deviation SD0 of the input signal from the first amplifier 70, which is the reference signal, is equal to or less than a predetermined value (S120). For example, it is determined whether the standard deviation SD0 has a value of zero or a value close to zero. As illustrated in FIG. 9, the reference signal has a certain level of value even where the subject is not lying on the mattress M. The standard deviation SD0 indicates a value from 1.3 to 4.9 as illustrated in FIG. 22. However, where disconnection occurs in the sensor unit 2 or where the mattress M has a failure, the reference signal changes little as illustrated in FIG. 13 and the standard deviation SD0 becomes approximately zero as illustrated in FIG. 23. That is, where the standard deviation SD0 of the reference signal has a value of zero or a value close to zero (YES in S120), it is assumed that the sensor unit 2 is in a failure state such as disconnection or the mattress M has a failure. Accordingly, the fail flag is set (S130) and the sensor sensitivity checking process is terminated.

When the standard deviation SD0 has a value not equal to or less than the predetermined value (NO in S120), it is assumed that the sensor unit 2 does not have a failure such as disconnection or the mattress M does not have a failure. Accordingly, the sensor sensitivity checking process carries on. In the embodiment, ratios of the standard deviations SD1, SD2, and SD3 of the respective input signals with the reference signal of the standard deviation SD0 are calculated (S140).

The standard deviation indicates a variation degree of the input signal from each amplifier. When the input signal of each amplifier is not saturated, the ratio of the standard deviation has a value at the same level of a ratio of the amplification factor (gain) of each amplifier. However, when the ratio of the standard deviation is different from the ratio of the amplification factor (gain) of the amplifier, the input signal of the amplifier is assumed to be saturated. Therefore, in the embodiment, the ratio of the standard deviation is calculated and it is determined whether the ratio of the standard deviation is within a specified value with respect to the ratio of the amplification factor (gain) of the amplifier. This allows using the signal of the amplifier with the highest amplification factor (gain) that is not saturated.

Figure 8:
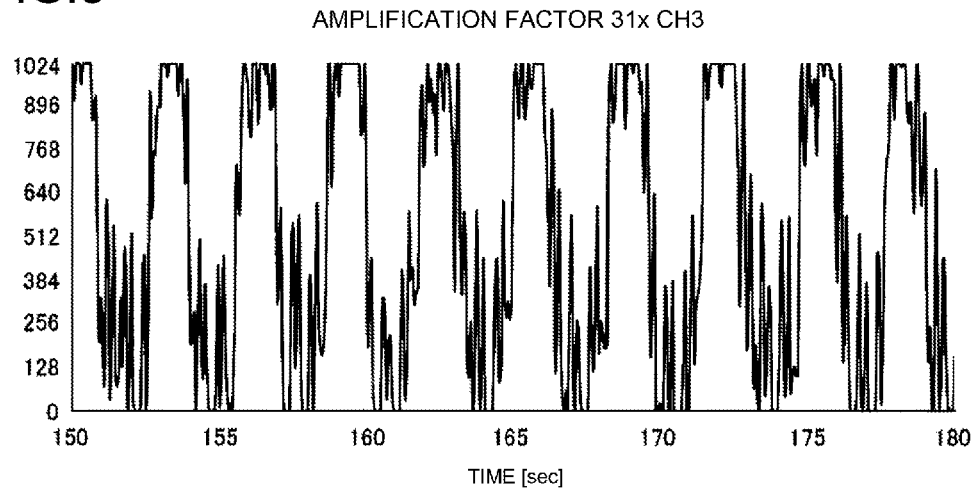
FIG. 8 is a graph illustrating an exemplary transition of an input signal from a fourth amplifier where the subject is in bed.

FIG. 21 illustrates values of the ratios of the standard deviations SD1, SD2, and SD3 with the standard deviation SD0 for each certain period of time (30 seconds) in the cases of FIG. 8 (where the subject is lying on the mattress M). FIG. 22 illustrates values of the ratios of the standard deviations SD1, SD2, and SD3 with the standard deviation SD0 for each certain period of time (30 seconds) in the cases of FIGS. 9-12 (where the subject is not lying on the mattress M). FIG. 23 illustrates values of the ratios of the standard deviations SD1, SD2, and SD3 with the standard deviation SD0 for each certain period of time (30 seconds) in the cases of FIGS. 13-16 (where the sensor unit 2 has a failure such as disconnection). FIG. 24 illustrates values of the ratios of the standard deviations SD1, SD2, and SD3 with the standard deviation SD0 for each certain period of time (30 seconds) in cases of FIGS. 17-20 (in abnormal cases with heavy vibration).

In the sensor sensitivity checking process of the embodiment, it is determined whether the ratio of the standard deviation SD3 of the input signal from the fourth amplifier 73 with the largest amplification factor (gain), to the reference signal of the standard deviation SD0, is within a specified value (for example, within ±10%), that is, whether or not the ratio of the standard deviation SD3 is at the same level as the ratio of the amplification factor (gain) of the fourth amplifier 73 with the amplification factor (gain) of the first amplifier 70 (S150).

As illustrated in FIG. 8, when the input signal from the fourth amplifier 73 is saturated, the ratio of the standard deviation SD3 to the reference signal of the standard deviation SD0 has, as illustrated in FIG. 21, a value smaller than 31 that is the ratio of the amplification factor (gain). This value is not within the specified value (for example, within ±10%). In this case, the process proceeds to next determination of the ratio of the standard deviation SD2. However, when the ratio of the standard deviation SD3 to the standard deviation SD0 has a value within the specified value (for example, within ±10%) with respect to 31 that is the ratio of the amplification factor (gain), the input signal from the fourth amplifier 73 to be input to the input port CH3 is determined as a signal to be used for a biological information detection process (S160). The sensor sensitivity checking process is then terminated.

Figure 7:
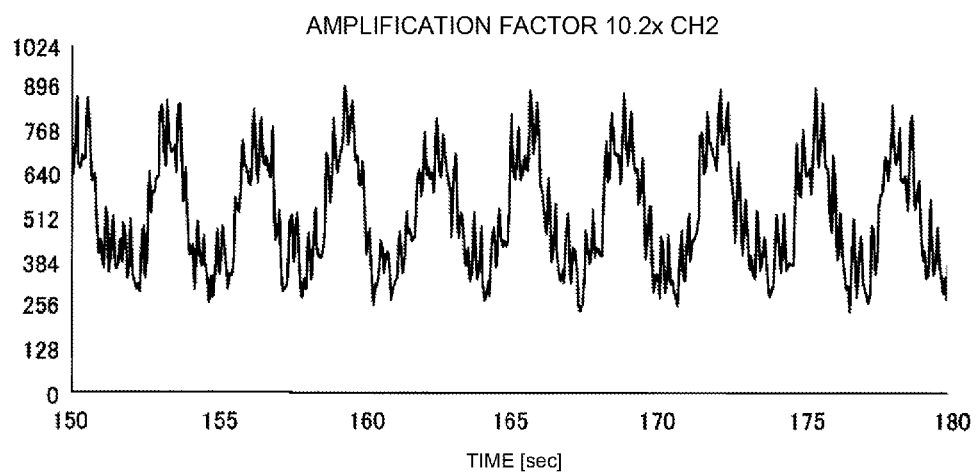
FIG. 7 is a graph illustrating an exemplary transition of an input signal from a third amplifier where the subject is in bed.

When the ratio of the standard deviation SD3 with the standard deviation SD0 is not within the specified value with respect to 31 that is the ratio of the amplification factor (gain), it is determined whether the ratio of the standard deviation SD2 to the standard deviation SD0 has a value within the specified value with respect to 10.2 that is the ratio of the amplification factor (gain) of the third amplifier 72 to the amplification factor (gain) of the first amplifier 70 (S170). For example, as illustrated in FIG. 7, when the input signal from the third amplifier 72 is not saturated, as illustrated in FIG. 21, the value of the ratio of the standard deviation SD2 with the standard deviation SD0 is a value within the specified value with respect to 10.2 that is the ratio of the amplification factors (gains). In this case, the input signal from the third amplifier 72 to be input to the input port CH2 is determined as a signal to be used for the biological information detection process (S180). The sensor sensitivity checking process is then terminated.

Figure 6:
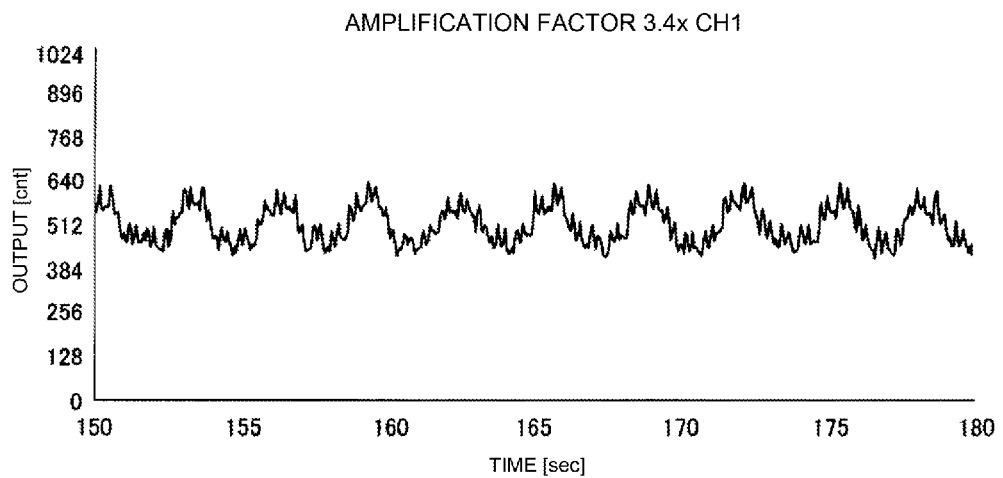
FIG. 6 is a graph illustrating an exemplary transition of an input signal from a second amplifier where the subject is in bed.

However, when the value of the ratio of the standard deviation SD2 with the standard deviation SD0 is not a value within the specified value with respect to 10.2 that is the ratio of the amplification factors (gains), it is determined whether the ratio of the standard deviation SD1 to the standard deviation SD0 has a value within the specified value with respect to 3.4 that is the ratio of the amplification factor (gain) of the second amplifier 71 to the amplification factor (gain) of the first amplifier 70 (S190). For example, as illustrated in FIG. 6, when the input signal from the second amplifier 71 is not saturated, as illustrated in FIG. 21, the value of the ratio of the standard deviation SD1 to the standard deviation SD0 is a value within the specified value with respect to 3.4 that is the ratio of the amplification factors (gains). In this case, the input signal from the second amplifier 71 to be input to the input port CH1 is determined as a signal to be used for the biological information detection process (S200). The sensor sensitivity checking process is then terminated.

As described above, as a determination result for the values of the ratios of standard deviations SD3, SD2, and SD1 to the standard deviation SD0, when all the ratios do not have values within the specified value with respect to the respective ratios of the amplification factors (gains), it is assumed that the sensor unit 2 or the mattress M has a failure. Accordingly, the fail flag is set (S210) and the sensor sensitivity checking process is terminated. For example, as illustrated in FIGS. 17-20, when all input signals change too quickly, all the ratios of the standard deviations SD3, SD2, and SD1 to the standard deviation SD0 do not have, as illustrated in FIG. 24, values within the specified value with respect to the respective ratios of the amplification factors (gains). In this case, the sensor unit 2 or the mattress M is assumed to be inappropriate for the measurement due to its abnormal state. Accordingly, the fail flag is set. The sensor sensitivity checking process as described above is performed, as illustrated in FIG. 3, for each certain period of time (for example, 30 seconds). Until approximately 90 seconds has elapsed immediately after the power supply of the sleep state measuring apparatus 1 is turned on, the subject frequently makes large movements while trying to sleep on the mattress M. Therefore, change in output signal of the sensor unit 2 is not stabilized. Accordingly, until approximately 90 seconds has elapsed immediately after the power supply of the sleep state measuring apparatus 1 is turned on, the sensor sensitivity checking process may not be performed and afterward the sensor sensitivity checking process may be performed.

When a direct output value is used to check a state of the output signal of the sensor unit 2, it is necessary to individually set the reference value and the threshold value, depending on a kind of sensor, a shape of the mattress M, a state of content in the mattress M, a circuit performance, and/or a resolution of the AD converting unit. However, according to the present embodiment, a failure such as disconnection of the sensor unit 2 is determined based on the standard deviation of the input signal corresponding to the output signal of the sensor unit 2, or the optimal amplification factor is determined based on the ratio of the standard deviation. Accordingly, according to the present embodiment, appropriate determination is performed without performing the above-described individual settings for the reference value and the threshold value.

In the embodiment, the optimal sensor sensitivity (the amplification factor, the gain) is set for each certain period of time (for example, 30 seconds). Accordingly, even when the subject, the mattress, the installation site, and a similar condition are changed, the embodiment allows performing appropriate determination without performing special setting or special adjustment.

The determination for a failure of the sensor or a failure state of the sensor or the mattress is also performed for each certain period of time (for example, 30 seconds) based on the standard deviation or the ratio of the standard deviation. Even when the measuring condition has been changed or aged deterioration occurs, according to the embodiment, it is possible to perform appropriate determination for a failure state. When a failure state has occurred, notification to the display unit and the external output unit are performed so that the measurement may be immediately stopped. This avoids unnecessary data acquisition, thus preventing incorrect determination.

Modifications

The above-described embodiment may be variously modified. Specific aspects of modifications are described below as examples. Any aspects equal to or more than two selected from the following examples may be combined as necessary insofar as the examples are not in conflict with one another.

(1) Modification 1

Figure 25:
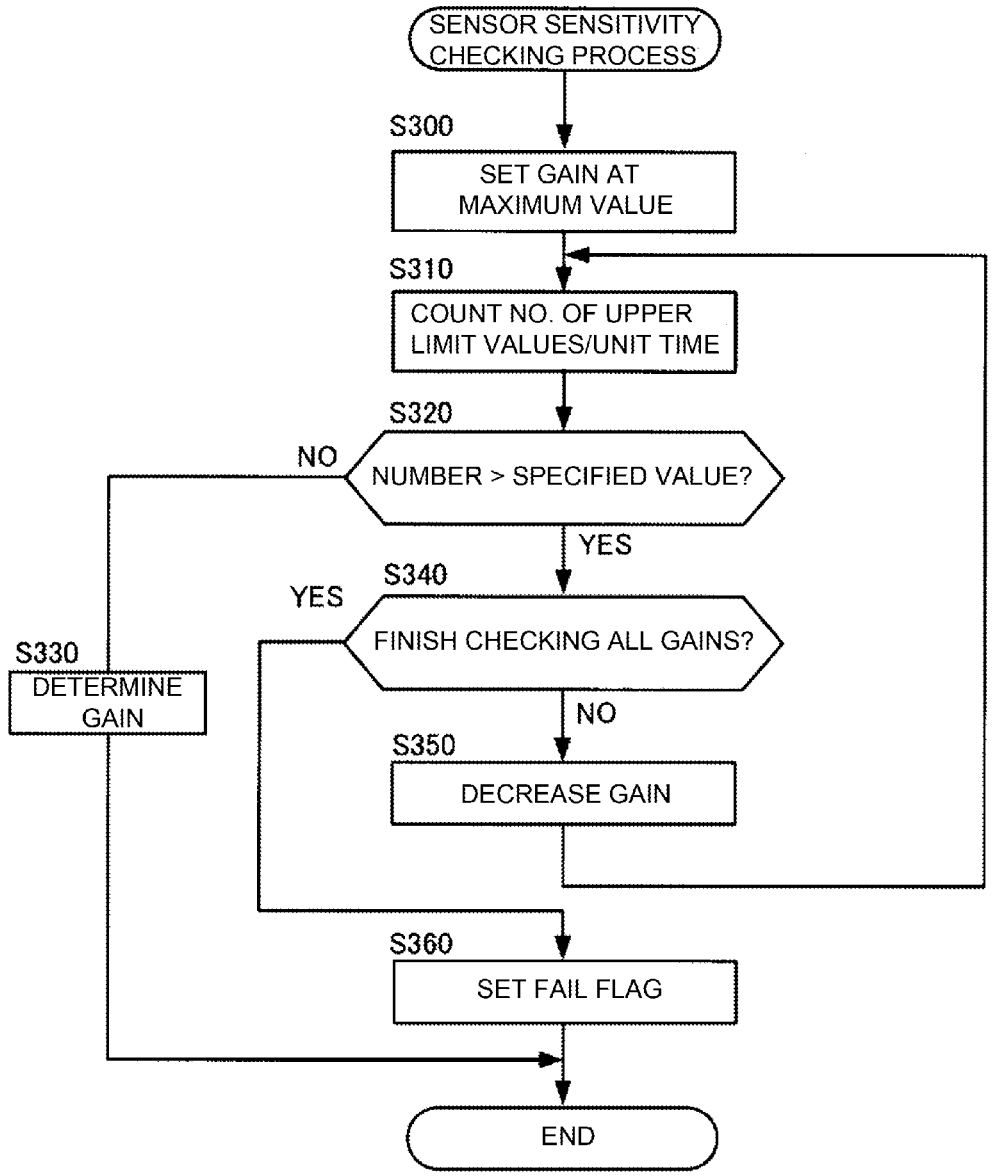
FIG. 25 is a flowchart illustrating a sensor sensitivity checking operation in a sleep state measuring apparatus according to a modification of the present invention.

While in the above-described embodiment, the example that includes a plurality of amplifiers with the amplification factors different from one another and a plurality of AD converting units corresponding to the amplifiers is described, the present invention is not limited to this example. For example, the embodiment may include one amplifier with a switchable amplification factor, and may perform the sensor sensitivity checking process described above while switching the amplification factors. The example will be described by referring to a flowchart of FIG. 25.

First, an amplification factor (gain) of the amplifier is set to the maximum value (S300). Subsequently, the number of input signals from the amplifier with the upper limit value per unit time is counted (S310). The upper limit value is set to a value where the input signal is assumed to be saturated. It is determined whether the number of the input signals from the amplifier with the upper limit value per unit time exceeds a specified value (S320). When the number does not exceed the specified value (NO in S320), the signal is assumed not to be saturated with the gain. Accordingly, as a gain of the signal to be used for the biological information detection process, the gain is determined to be used (S330).

However, where the number of input signals from the amplifier with the upper limit value per unit time exceeds the specified value, the input signal is assumed to be saturated. Accordingly, the gain is switched and the same process is performed. However, when the number of input signals from the amplifier with the upper limit value per unit time exceeds the specified value regarding all the gains to be switchable (YES in S340), it is assumed that some failure occurs and the state is inappropriate for the measurement. Accordingly, the fail flag is set (S360) and the process is terminated.

Where the gain can be switched, the gain is switched to a gain at the next smaller level (S350). Hereinafter, similarly, it is determined whether the number of input signals from the amplifier with the upper limit value per unit time exceeds the specified value.

This configuration may also allow automatic setting for the optimal sensor sensitivity and automatic determination for a failure of the sensor or similar member. In the case of the configuration, when a failure such as disconnection of the sensor is determined, the gain is set to the minimum value to simply determine whether the number of input signals from the amplifier with the lower limit value per unit time exceeds a specified value. The lower limit value in this case is simply set to a value smaller than values which change even where the subject is not lying on the mattress M.

(2) Modification 2

While in the above-described embodiment, the example where the amplifiers have the respective amplification factors of 1×, 3.4×, 10.2×, and 31× is described, the present invention is not limited to this example. The amplification factors may be changed as necessary. While in the above-described embodiment, the example using the four amplifiers is described, the number of the amplifiers may also be changed as necessary. While in the above-described embodiment, the example where the certain period to perform the data acquisition and the process is 30 seconds, the certain period of time may also be changed as necessary. The value of the specified value used in the sensor sensitivity checking process may also be changed as necessary.

(3) Modification 3

The application of the biological signal processor according to the embodiments is not limited to the sleep state measuring apparatus. For example, for beds in a hospital or a nursing home, the biological signal processor may be used alone and utilized to determine that a patient or a care-receiver is in bed (getting into bed and getting out of bed). The biological signal processor according to the embodiments may be applied to other devices such as a wake-up device.

(3) Modification 3

While in the above-described embodiment, the first AD converting unit 80 to the fourth AD converting unit 83 are disposed in the AD converting unit 8, each AD converting unit may be arranged in any portion. For example, the AD converting unit may be disposed in the signal processing unit 7 or may be disposed in the CPU 9. While in the above-described embodiment, the measurement signal is amplified and then the AD conversion is performed, the measurement signal may be amplified after the AD conversion.

(5) Modification 5

While in the above-described embodiment, the standard deviation is used as the measure that indicates variation degree of the input signal (the output signal), any variation measure may be used. For example, a dispersion of the input signal (the output signal) or a variation coefficient (a value obtained by dividing a standard deviation by a mean value of the group) of the level value may be used as variation measure.

(6) Modification 6

The above-described embodiment may be modified as an embodiment where the CPU 9 collaborates with a real-time clock (RTC) to measure elapsed time. In the embodiment, when electric power is not supplied to the RTC from the power supply 11, supplying electric power from a secondary power supply allows continuing to measure elapsed time even when power supply from the power supply 11 is stopped. The above-described embodiment may be modified as an embodiment using one microcomputer instead of the CPU 9 and the storage unit 10. The above-described embodiment may be modified as an embodiment using a piezoelectric element such as a piezo cable, a capacitance sensor, a light receiving element, a film sensor, a strain gauge, or similar sensor instead of a capacitor microphone sensor.

The preceding description has been presented only to illustrate and describe exemplary embodiments of the present biological signal processor. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A biological signal processor comprising:
   a sensor unit that is usable with a mattress, measures biological displacement of a subject on the mattress, and outputs a measurement signal indicative of a measurement result;
   a signal processing unit that amplifies the measurement signal with a plurality of different gains and outputs respective output signals;
   an AD converting unit that performs AD conversion on the respective output signals to obtain level values and outputs the respective level values; and
   a determining unit that determines an output signal to be used for detecting biological information among the respective output signals, wherein
   the determining unit uses the level value corresponding to the output signal amplified with the minimum gain among the respective level value as a reference value, and calculate a ratio of a variation measure indicative of variation degree in a level value corresponding to an output signal amplified with another gain to the variation measure indicative of variation, degree, in the reference value, and
   in case where a ratio of a variation measure indicative of variation decree in a level value corresponding to an output signal amplified with a predetermined gain to the variation measure indicative of the variation decree in the reference value is within a predetermined value range with respect to a ratio of the predetermined gain to the minimum gain, the determining unit employs the output signal amplified with the predetermined gain as the output signal to be used for detecting the biological information.

2. The biological signal processor according to claim 1, wherein in case where the ratio of the variation measure indicative of the variation degree in level value corresponding to the output signal amplified with each gain is not within the predetermined value range regarding the ratio of each gain with the minimum gain, the determining unit determines that the sensor unit is abnormal.

3. The biological signal processor according to claim 1, further comprising
   a detection unit that performs a biological information detection process based on an output signal of the signal processing unit employed by the determining unit.

4. The biological signal processor according to claim 1, wherein the signal processing unit includes a plurality of analog circuits.

5. The biological signal processor according to claim 1, wherein the signal processing unit includes an analog circuit switchable between different gains.

6. The biological signal processor according to claim 1, wherein the variation measure indicative of the variation degree is a standard deviation.

7. The biological signal processor according to claim 1, wherein the determining unit determines that the sensor unit is in an abnormal condition in case where a variation measure is equal to or less than a predetermined value, the variation measure being indicative of variation degree in a level value corresponding to an output signal amplified with a minimum gain among the respective level values.

8. A biological signal processor comprising:
   a sensor unit that is usable with a mattress, measures biological displacement of a subject on the mattress, and outputs a measurement signal indicative of a measurement result;
   a signal processing unit that amplifies the measurement signal with a plurality of different gains and outputs respective output signals;
   an AD converting unit that performs AD conversion on the respective output signals to obtain level values and outputs the respective level values; and
   a determining unit that determines that the sensor unit is in an abnormal condition based on whether the number of the level values corresponding to an output signal amplified with a minimum gain among the plurality of different gains, which reach a lower limit value per unit time exceeds a specified value,
   wherein the lower limit value is set to a value smaller than any of values which can be detected when the subject is not lying on the mattress.

9. The biological signal processor according to claim 8, wherein the determining unit employs an output signal amplified with a predetermined gain among the respective output signals as an output signal of the signal processing unit in case where the number of the level values corresponding to the output signal amplified with the predetermined gain, which reach an upper limit value per unit time falls below a specified value.

10. The biological signal processor according to claim 9, wherein the determining unit determines that the sensor unit is in an abnormal condition in case where the number of level values corresponding to any of the respective output signals, which reach an upper limit value per unit time exceeds a specified value.

* * * * *